United States Patent [19]
Kohr

[11] Patent Number: 5,676,733
[45] Date of Patent: Oct. 14, 1997

[54] METHOD FOR RECOVERING METAL VALUES FROM CONCENTRATES OF SULFIDE MINERALS

[75] Inventor: William J. Kohr, San Mateo, Calif.

[73] Assignee: Geobiotics, Inc., Hayward, Calif.

[21] Appl. No.: 476,444

[22] Filed: Jun. 7, 1995

Related U.S. Application Data

[63] Continuation-in-part of Ser. No. 343,888, Nov. 16, 1994, Pat. No. 5,573,575, which is a continuation-in-part of Ser. No. 161,742, Dec. 3, 1993, Pat. No. 5,431,717.

[51] Int. Cl.[6] .................................................. C22B 3/18
[52] U.S. Cl. ........................ 75/712; 75/744; 423/DIG. 17
[58] Field of Search ...................... 423/DIG. 17; 75/712, 75/744

[56] References Cited

U.S. PATENT DOCUMENTS

| | | | |
|---|---|---|---|
| 3,647,261 | 3/1972 | Stenger et al. | 299/4 |
| 4,017,309 | 4/1977 | Johnson | 299/5 |
| 5,332,559 | 7/1994 | Brierley et al. | 423/DIG. 17 |

Primary Examiner—Melvyn Andrews
Attorney, Agent, or Firm—Lyon & Lyon LLP

[57] ABSTRACT

A method of recovering precious metal values from refractory sulfide ores is provided. The method includes the steps of separating clays and fines from a crushed refractory sulfide ore, forming a heap from the refractory sulfide ore, producing a concentrate of refractory sulfide minerals from the separated fines and adding the concentrate to the heap, bioleaching the heap to thereby oxidize iron sulfides contained therein, and hydrometallurgically treating the bioleached ore to recover precious metal values contained therein.

25 Claims, 5 Drawing Sheets

METHOD FOR RECOVERING METAL VALUES FROM CONCENTRATES OF SULFIDE MINERALS

This is a continuation-in-part of application Ser. No. 08/343,888, filed on Nov. 16, 1994, now U.S. Pat. No. 5,573,575, which is a continuation-in-part of application Ser. No. 08/161,742, filed on Dec. 3, 1993, now U.S. Pat. No. 5,431,717.

BACKGROUND OF THE INVENTION

1. Field of the Invention

The present invention relates to the recovery of metal values from refractory sulfide and refractory carbonaceous sulfide ores.

2. Description of the Prior Art

Gold is one of the rarest metals on earth. Gold ores can be categorized into two types: free milling and refractory. Free milling ores are those that can be processed by simple gravity techniques or direct cyanidation. Refractory ores, on the other hand, are not amenable to conventional cyanidation treatment. Such ores are often refractory because of their excessive content of metallic sulfides (e.g., pyrite) and/or organic carbonaceous matter.

A large number of refractory ores consist of ores with a precious metal such as gold occluded in iron sulfide particles. The iron sulfide particles consist principally of pyrite and arsenopyrite. Precious metal values are frequently occluded within the sulfide mineral. For example, gold often occurs as finely disseminated sub-microscopic particles within a refractory sulfide host of pyrite or arsenopyrite. If the gold remains occluded within the sulfide host, even after grinding, then the sulfides must be oxidized to liberate the encapsulated precious metal values and make them amenable to a leaching agent (or lixiviant).

A number of processes for oxidizing the sulfide minerals to liberate the precious metal values are well known in the art. One known method of oxidizing the metal sulfides in the ore is to use bacteria, such as *Thiobacillus ferrooxidans*, Sulfolobus, Acidianus species and facultative-thermophilic bacteria in a microbial pretreatment. The foregoing microorganisms oxidize the iron sulfide particles to cause the solubilization of iron as ferric iron, and sulfide, as sulfate ion.

If the refractory ore being processed is a carbonaceous sulfide ore, then additional process steps may be required following microbial pretreatment to prevent preg-robbing of the aurocyanide complex or other precious metal-lixiviant complexes by the native carbonaceous matter upon treatment with a lixiviant.

As used herein, sulfide ore or refractory sulfide ore will be understood to also encompass refractory carbonaceous sulfide ores.

A known method of bioleaching carbonaceous sulfide ores is disclosed in U.S. Pat. No. 4,729,788, issued Mar. 8, 1988, which is hereby incorporated by reference. According to the disclosed process, thermophilic bacteria, such as Sulfolobus and facultative-thermophilic bacteria, are used to oxidize the sulfide constituents of the ore. The bioleached ore is then treated with a blanking agent to inhibit the preg-robbing propensity of the carbonaceous component of the ore. The precious metals are then extracted from the ore using a conventional lixiviant of cyanide or thiourea.

Another known method of bioleaching carbonaceous sulfide ores is disclosed in U.S. Pat. No. 5,127,942, issued Jul. 7, 1992, which is hereby incorporated by reference. According to this method, the ore is subjected to an oxidative bioleach to oxidize the sulfide component of the ore and liberate the precious metal values. The ore is then inoculated with a bacterial consortium in the presence of nutrients therefor to promote the growth of the bacterial consortium, the bacterial consortium being characterized by the property of deactivating the preg-robbing propensity of the carbonaceous matter in the ore. In other words, the bacterial consortium functions as a biological blanking agent. Following treatment with the microbial consortium capable of deactivating the precious-metal-adsorbing carbon, the ore is then leached with an appropriate lixiviant to cause the dissolution of the precious metal in the ore.

Problems exist, however, with employing bioleaching processes in a heap leaching environment. These include nutrient access, air access, and carbon dioxide access for making the process more efficient and thus an attractive treatment option. Moreover, for biooxidation, the induction times concerning biooxidants, the growth cycles, viability of the bacteria and the like are important considerations because the variables such as accessibility, particle size, settling, compaction and the like are economically irreversible once a heap has been constructed. As a result, heaps cannot be repaired once formed, except on a limited basis.

Ores that have a high clay and/or fines content are especially problematic when processing in a heap leaching or heap biooxidation process. The reason for this is that the clay and/or fines can migrate through the heap and plug channels of air and liquid flow, resulting in puddling; channelling; nutrient-, carbon dioxide-, or oxygen-starving; uneven biooxidant distribution, and the like. As a result, large areas of the heap may be blinded off and ineffectively leached. This is a common problem in cyanide leaching and has lead to processes of particle agglomeration with cement for high pH cyanide leaching and with polymers for low pH bioleaching. Polymer agglomerate aids may also be used in high pH environments, which are customarily used for leaching the precious metals, following oxidative bioleaching of the iron sulfides in the ore.

Biooxidation of refractory sulfide ores is especially sensitive to blocked percolation channels by loose clay and fine material because the bacteria need large amounts of air or oxygen to grow and biooxidize the iron sulfide particles in the ore. Air flow is also important to dissipate heat generated by the exothermic biooxidation reaction, because excessive heat can kill the growing bacteria in a large, poorly ventilated heap.

Ores that are low in sulfide or pyrite, or ores that are high in acid consuming materials such as calcium carbonate or other carbonates, may also be problematic when processing in a heap biooxidation. The reason for this is that the acid generated by these low pyrite ores is insufficient to maintain a low pH and high iron concentrate needed for bacteria growth.

A need exists, therefore, for a heap bioleaching technique that can be used to biooxidize precious metal bearing refractory sulfide ores and which provides improved air and fluid flow within the heap. In addition, a need exists for a heap bioleaching process in which ores that are low in sulfide minerals, or ores that are high in acid consuming materials such as calcium carbonate, may be processed.

A need also exists for a biooxidation process which can be used to liberate occluded precious metals in concentrates of refractory sulfide minerals. Mill processes that can be used for oxidizing such concentrates include bioleaching in a stirred bioreactor, pressure oxidation in an autoclave, and roasting. These mill processes oxidize the sulfide minerals in the concentrate relatively quickly, thereby liberating the entrapped precious metals. However, unless the concentrate has a high concentration of gold, it does not economically justify the capital expense or high operating costs associated with these processes. And, while a mill bioleaching process is the least expensive mill process in terms of both the initial capital costs and its operating costs, it still does not justify processing concentrates having less than about 0.5 oz. of gold per ton of concentrate, which typically requires an ore having a concentration greater than about 0.07 oz. of gold per ton. Therefore, a need also exists for a process that can be used to biooxidize concentrates of precious metal bearing refractory sulfide minerals at a rate comparable to a stirred tank bioreactor, but that has capital and operating costs more comparable to that of a heap bioleaching process.

In addition to concentrates of precious metal bearing sulfide minerals, there are many sulfide ores that contain metal sulfide minerals that can potentially be treated using a biooxidation process. For example, many copper ores contain copper sulfide minerals. Other examples include zinc ores, nickel ores, and uranium ores. Biooxidation could be used to cause the dissolution of metal values such as copper, zinc, nickel and uranium from concentrates of these ores. The dissolved metal values could then be recovered using known solvent extraction techniques, iron cementation, and precipitation. However, due to the sheer volume of the sulfide concentrate formed from sulfide ores, a stirred bioreactor would be prohibitively expensive, and standard heap operations would simply take too long to make it economically feasible to recover the desired metal values. A need also exists, therefore, for an economical process for biooxidizing concentrates of metal sulfide minerals produced from sulfide ores to thereby cause the dissolution of the metal values so that they may be subsequently recovered from the bioleachate solution.

SUMMARY OF INVENTION

It is an object of one aspect of the present invention to provide a heap bioleaching process of the type described above, wherein the refractory sulfide ore is rendered more susceptible to biooxidation, thereby providing improved recovery of the precious metal values contained within the ore. The method of the present invention achieves this object by removing the clays and/or fines from the refractory sulfide ore after it is crushed to a size appropriate for a heap leaching process. The heap may then be formed without concern of the air and liquid flow channels in the heap becoming plugged. Further, if the separated clay and/or fine material has a sufficiently high precious metal content, it may be separately treated to recover the precious metal values contained therein.

In another aspect of the present invention, a process for recovering precious metal values from concentrates of precious metal bearing refractory sulfide minerals is provided. The process comprises the steps of (a) distributing a concentrate of refractory sulfide minerals on top of a heap of support material; (b.) biooxidizing the concentrate of refractory sulfide minerals; (c.) leaching precious metal values from the biooxidized refractory sulfide minerals with a lixiviant; and (d.) recovering precious metal values from the lixiviant. An advantage of this process is that the rate at which the sulfide minerals biooxidize is much higher than would be observed in a traditional heap bioleaching operation. Despite this high rate of biooxidation, however, the initial capital costs and operating costs for the disclosed process are lower than that associated with a mill type biooxidation process.

Gold is the preferred precious metal recovered using the process according to the present aspect of the invention. However, other precious metals can also be recovered, including silver and platinum. The support material is preferably selected from the group consisting of lava rock, gravel, and coarsely ground ore. Lava rock is particularly preferred due to its high surface area. As those skilled in the art will immediately recognize, a number of lixiviants can be used in conjunction with the present process, however, thiourea and cyanide are the preferred, cyanide being a particularly preferred lixiviant.

In another aspect of the present invention a process is provided for recovering metal values from sulfide ores. Such ores include, by way of example, chalcopyrite, sphalorite, nickel sulfide ores, and uranium sulfide ores. The process according to this aspect of the invention comprises (a.) forming a concentrate of metal sulfide minerals; (b.) spreading the concentrate on top of a heap of support material; (c.) biooxidizing the concentrate; and (d.) recovering metal values from the solution used to biooxidize the metal sulfide minerals. Due to the fact that this process uses a heap of support material for the bioreactor, its capital and operating costs are less than that of a mill bioleaching operation. However, due to the good air flow in the heap, the biooxidation rate of the sulfide minerals is quite high and can approach that of what would be observed in a mill type operation.

Depending on the sulfide ore from which the concentrate is obtained, the metal values that can be recovered from the process according to the present aspect of the invention include copper, zinc, nickel and uranium. The support material used in the present process is preferably selected from the group consisting of lava rock, gravel, and coarsely ground rock. Lava rock is particularly preferred due to its high surface area.

The above and other objects, features and advantages will become apparent to those skilled in the art from the following description of the preferred embodiments.

DESCRIPTION OF THE PREFERRED EMBODIMENTS

Figure 1:
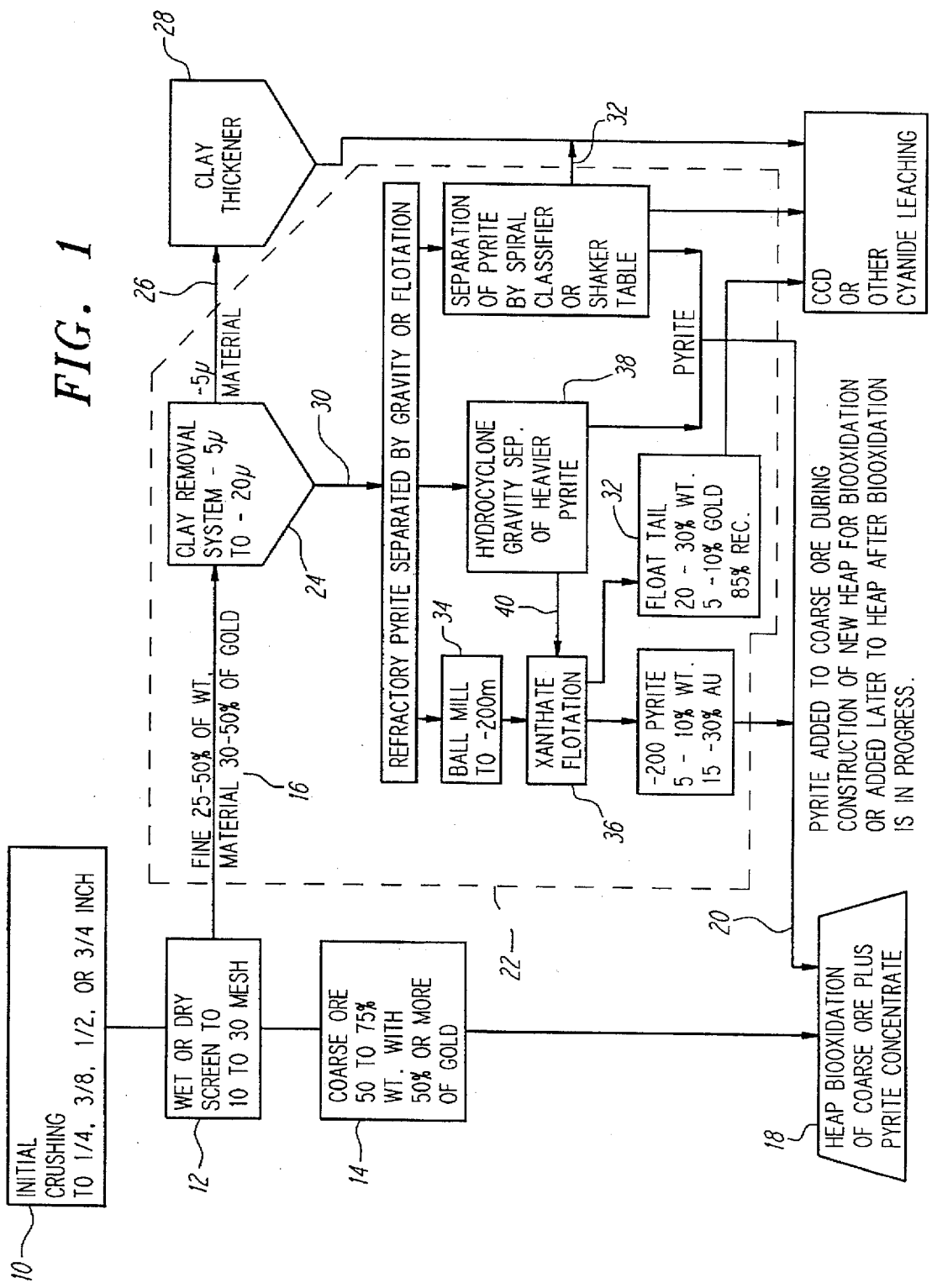
FIG. 1 is a schematic of a process flow sheet according to a preferred embodiment of the present invention.

According to one aspect of the present invention, refractory sulfide ores can be rendered more susceptible to biooxidation in a heap leaching process. This is accomplished by separating the clay and/or fine materials from the refractory sulfide ore after it has been crushed to a size appropriate for heap leaching. In the present embodiment the method of removal is wet size screening. It will be readily apparent to those skilled in the art, however, that any other method for separating the clay and/or fine material from the refractory ore may be used. For example, dry screening and cyclone classifying are well known to those skilled in the art.

By removing the fines and clays from the refractory sulfide ore, the air and liquid flow through the heap is improved. This will reduce the time required to sufficiently biooxidize the iron sulfide particles in the ore to liberate the precious metal values and make them amenable to subsequent lixiviation with cyanide or thiourea, preferably cyanide. In addition to faster biooxidation, in a well ventilated heap, having good fluid flow, it becomes more feasible to change the pH from an acidic pH of 1.0 to 2.0 that is best for biooxidation to a basic pH of 10.0 or more needed for cyanide leaching without remaking or restacking the heap.

The refractory sulfide ore is preferably crushed to a target maximum size in the range of approximately ¼ to 1 inch. Appropriate target maximum particle sizes include ¼, ⅜, ½, and 1 inch. If the ore will pass any of these target particle sizes, it should be amenable to heap leaching. The smaller the particle size, however, the greater the surface area of the sulfide particles in the ore and, of course, the faster the sulfide particles will be biooxidized. Increased recovery of the precious metal values should also result. This, however, must be weighed against the additional cost of crushing the ore to a smaller particle size. The additional amount of precious metal recovered may not justify the added cost.

Of course if the refractory sulfide ore body being treated is already an appropriate size for heap leaching, no additional crushing is required.

Fines are naturally produced during the crushing process. The size of the fines and clays removed from the crushed ore should be about minus 60 mesh as a minimum upper limit to about minus ⅛ inch as a maximum upper limit. After the clay and fines are separated from the bulk of the ore, a heap is formed with the ore. The heap may then be treated with a standard bioleaching process to oxidize the iron sulfide particles in the ore and liberate the occluded precious metal values, which are preferably gold. Because the majority of the clay and fine materials have been removed, obstruction of the air and liquid flow channels by these materials is no longer a concern, thereby improving percolation leaching of the ore.

After biooxidation, the precious metal in the pretreated ore can be extracted using a conventional lixiviant such as cyanide or thiourea, preferably cyanide. Of course, however, as a person of ordinary skill in the art would recognize, if the refractory sulfide ore is also refractory due to carbonaceous matter contained in the ore, additional processing steps must be employed to reduce the preg-robbing propensity of the ore prior to lixiviation. A number of such processes are well known in the art.

For example, the methods used in U.S. Pat. Nos. 4,729,788 and 5,127,942, both of which have already been incorporated herein by reference, can be used. Further, the microbial process for treating carbonaceous ores disclosed in U.S. Pat. No. 5,162,105, issued Nov. 10, 1992, hereby incorporated by reference, can also be used.

The fine material that has been separated may contain large amounts of precious metal values. Indeed the economic value of these metal values may be sufficiently high to justify further processing of these materials to recover the additional metal values. In a particularly preferred embodiment of the present invention, the separated fine material is further processed to recover at least a portion of the precious metal values contained therein.

To recover the precious metal values from the fine material, the fine material is preferably treated in a mill process to remove the iron sulfide particles from the clay and sand particles. The reason for this is that, as discussed above, precious metal values, especially gold, often occur as finely disseminated microscopic particles within the iron sulfide particles. These fine sulfide particles, therefore, frequently contain a significant portion of the overall precious metal values. Further, because a relatively high percentage of the precious metal values in the ore are associated with this fraction of the ore, they can be economically treated in a mill process.

As will be recognized by those skilled in the art, a variety of methods can be used to separate the iron sulfide particles from the remainder of the fines. These methods include, by way of example only, gravity separation and flotation. If desired, the iron sulfide particles can be subjected to additional grinding before flotation. Gravity separation techniques that can be used include shaker tables, hydrocyclones, and spiral classifiers.

The iron sulfide concentrate, if refractory, is preferably bioleached with bacteria in a tank or mill process to liberate the occluded precious metal values. Alternatively, the sulfide concentrate can be added back to the heap to allow for a slower heap biooxidation process. However, because these particles are typically larger and more hydrophobic than clay particles, they tend to stick more readily to the larger particles in the heap, and, thus, the problem of obstructed percolation channels is not encountered. The iron sulfide concentrate can also be treated by a variety of other methods well known in the art such as roasting, pressure oxidation, and chemical oxidation. Because the concentration of gold or other precious metal values is relatively high in this ore fraction and its overall volume small, all of these mill processes may be economically utilized.

If the iron sulfide concentrate is only partially refractory, then it can be directly leached with a lixiviant such as cyanide to remove the nonrefractory gold. The tail from this leaching process could then be washed free of cyanide and added to the heap for biooxidation to release the remaining refractory gold or other precious metal values.

The fine material removed from the refractory sulfide ore by size separation, and which has also had the iron sulfide particles removed from it, may still contain economic values of gold or other precious metals. Further, this fine material is likely to be less refractory than other iron sulfide material if the size has lead to oxidation. Therefore, agglomeration of this material with cement, or other agglomeration aids that can be used at a high pH, may provide good recoveries if leached with cyanide directly.

The fine material may have sufficient gold value in the case of high grade ore to merit a mill leaching process such as carbon-in-pulp or counter current decantation.

A more recently preferred embodiment of the present invention is now described in connection with the process flow sheet illustrated in FIG. 1.

As can be seen from referring to FIG. 1, a precious metal bearing refractory sulfide ore is preferably crushed to a target maximum size in the range of approximately ¼ to 1 inch at crushing station 10. Preferably the ore is crushed to a target maximum particle size of ¼, ⅜, ½, or ¾ inch. Of course, if the refractory sulfide ore body being treated is already of an appropriate size for heap leaching, no additional crushing is required.

As in the present embodiment, the precious metal to be recovered from the ore is typically gold. However, as those skilled in the art will readily recognize, the method according to the present invention is equally applicable to the recovery of other precious metals, including silver and platinum from refractory sulfide ores.

After the gold bearing refractory sulfide ore is crushed to the appropriate size, the fines in the ore are separated from the crushed ore at separation station 12. Preferably the fines are separated using a wet or dry screening process. To ensure good air and liquid flow in the heap, fines smaller than about 10 to 30 mesh (Tyler mesh series) should be separated out at separation station 12. The coarse fraction of the ore 14, that is the ore greater than about 10 to 30 mesh, will typically contain approximately 50% or more of the gold values in the entire ore and comprise about 50 to 75% of the weight of the ore. The fines 16 that have been separated out will typically contain approximately 30 to 50% of the gold values and comprise approximately 25 to 50% of the weight of the initial ore.

Because of the significant gold values typically contained in the fines 16, the fines are further processed to recover at least a portion of the precious metal values contained therein. This is preferably accomplished by producing a concentrate 20 of refractory pyrite minerals from the fines 16 in the pyrite concentration circuit 22. Pyrite concentrate 20 will typically comprise about 5 to 10% of the initial weight of the ore and about 15 to 30% of its gold values.

If the ore contains refractory arsenopyrite minerals, then refractory pyrite concentrate 20 will also contain these minerals.

Because, as a general rule, the pyrite particles in the pyrite concentrate 20 are larger and more hydrophobic than the clay particles found in fines 16, the pyrite concentrate 20 can be combined with the coarse fraction of the ore 14 during heap construction without significantly impeding fluid and air flow within the heap during bioleaching. This is because the pyrite particles in pyrite concentrate 20 will tend to stick to the larger particles in the coarse fraction of the ore, rather than migrating through the heap and causing blocked flow channels. Pyrite concentrate 20, may also be added to the top of the heap before or after the biooxidation process is already in progress.

The bacterial oxidation of pyrite generates ferrous sulfate and sulfuric acid in the net reaction summarized by Equation (1). This net reaction can be broken into two distinct reactions, Equations (2) and (3), where Equation (2) is the aerobic reaction catalyzed by bacterial activity and Equation (3) is the anaerobic reaction occurring at the surface of the sulfide mineral. Equation (4) is a similar anaerobic reaction occurring at the surface of arsenopyrite minerals.

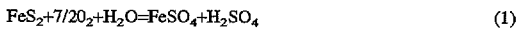

$$FeS_2+7/2O_2+H_2O=FeSO_4+H_2SO_4 \quad (1)$$

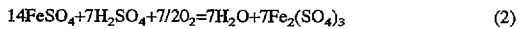

$$14FeSO_4+7H_2SO_4+7/2O_2=7H_2O+7Fe_2(SO_4)_3 \quad (2)$$

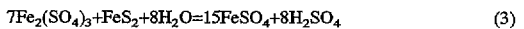

$$7Fe_2(SO_4)_3+FeS_2+8H_2O=15FeSO_4+8H_2SO_4 \quad (3)$$

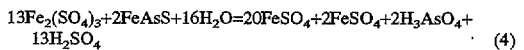

$$13Fe_2(SO_4)_3+2FeAsS+16H_2O=20FeSO_4+2FeSO_4+2H_3AsO_4+13H_2SO_4 \quad (4)$$

An advantage of adding pyrite concentrate 20 to heap 18 is that this fine milled pyrite is more readily oxidized than the pyrite mineral particles found in coarse ore 14; thus, the acid produced from the oxidation of the pyrite concentrate can be used to help lower the pH of the coarse ore in the heap more quickly. This is especially valuable when dealing with ores that are high in acid consuming materials such as calcium carbonate or other carbonates. Further, by adding the pyrite concentrate to the top of heap 18, ferric ions produced during its biooxidation will migrate to the lower part of the heap where bacterial growth may be inhibited due to toxins, which have not been washed from the ore early in the biooxidation process, or due to the lack of oxygen. As a result, biooxidation of the pyrite minerals in the lower part of the heap will proceed even if bacterial growth is not favored in this region.

There is also an advantage to adding pyrite concentrate 20 to a heap 18 that has been undergoing biooxidation for a long period of time. In the later stages of biooxidation most of the exposed and reactive sulfides will have already been oxidized, resulting in a slow down in the rate of biooxidation. This slow down in the rate of biooxidation can lead to a drop in iron levels and an increase in pH within heap 18. Addition of a reactive sulfide concentrate can restart an active biooxidation process that can increase indirect chemical leaching of imbedded sulfide minerals due to the high ferric levels produced from the biooxidation of the sulfide concentrate.

The preferred methods of producing pyrite concentrate 20 are explained in detail below in connection with pyrite concentration circuit 22.

After heap 18 is constructed, it may be pretreated using a standard heap biooxidation process to oxidize the iron sulfide particles in the ore and liberate the occluded precious metal values. And, because the majority of the clay and fine materials have been removed, obstruction of the air and liquid flow channels by these materials is significantly reduced, resulting in improved percolation leaching of the ore.

If the bioleachate solution is recycled during the biooxidation process, the biooxidation rate can be improved by using the method of solution management disclosed in the U.S. patent application Ser. No. 08/329,002, entitled "Method For Improving The Heap Biooxidation Rate Of Refractory Sulfide Ore Particles That Are Biooxidized Using Recycled Bioleachate Solution," which was filed Oct. 25, 1994, by William J. Kohr, Chris Johannson, John Shield, and Vandy Shrader, the text of which is incorporated herein by reference as if fully set forth.

Referring again to FIG. 1, pyrite concentration circuit 22 is now described. Three preferred methods of producing pyrite concentrate 20 are illustrated within pyrite concentration circuit 22. These methods may be used in combination or in the alternative.

The fines 16 will typically comprise very fine clay particles, which are typically less than 5 to 20 μm; sand particles; and refractory sulfide particles. The clay particles are very small and very hydrophilic in comparison to the sand and refractory sulfide particles, making them particularly deleterious to heap bioleaching processes, because they tend to migrate through the heap and plug flow channels as they swell from the absorption of water. The clay particles are, therefore, preferably removed from the fines 16 so that a concentrate of refractory sulfide particles can be produced that can be safely added to heap 18 with minimal obstruction of the flow channels in the heap. Thus, as illustrated in FIG. 1, the first step in each of the preferred methods of producing pyrite concentrate 20 is the removal of the clay particles from the fines using clay removal system 24, which is preferably a hydrocyclone or a settling tank. Of course, however, if the ore is a low clay bearing ore, this step may be omitted.

The set point for the maximum size particle removed in clay removal system 24 will depend on the distribution of clay particle sizes within fines 16. If the set point for the clay removal system is set at less than about 10 μm, a settling tank is the preferred removal method of separation because hydrocyclones cannot currently make efficient separations between particle sizes of less than about 10 μm.

In a high clay ore, clay material 26 separated from the fines 16 will typically comprise about 10% of the initial weight of the ore and about 5 to 10% of its gold values. Further, because of its low refractory nature, clay material 26 may be further processed to recover the gold values it contains using a traditional cyanide mill leaching process such as counter current decantation or carbon-in-pulp. Before processing clay material 26 in one of these traditional cyanide mill leaching processes, however, the pulp density of the clay material should be increased using a thickener 28 until a pulp density of about 30 to 40% is achieved.

After the clays have been removed from the fines 16, the refractory pyrite particles are also separated out to form refractory pyrite concentrate 20, which can be added to heap 18 as explained above. The refractory pyrite particles are preferably separated from clay depleted fines 30 using flotation or a gravity separation technique.

Three preferred methods for separating the refractory sulfide particles from the clay depleted fines 30 are now described. The first method entails fine grinding the clay depleted fines 16 until a particle size of less than about –200 mesh is achieved. This is preferably accomplished in ball mill 34. The refractory pyrite materials are then removed from the material 30 using a flotation cell 36 with a xanthate collector. The floated pyrite material from flotation cell 36 forms the pyrite concentrate 20.

A second method of producing pyrite concentrate 20 from material 30 comprises separating material 30 into two fractions using a hydrocyclone 38: the first, comprising –200 mesh material 40, and the second comprising coarse sand particles, which are greater than about 200 mesh, and heavier pyrite particles. The material which is less than 200 mesh is further treated in xanthate flotation cell 36 to remove refractory sulfides. The floated refractory sulfides and the coarse sand particles and heavier pyrite are then recombined to form pyrite concentrate 20. This method differs from the first pyrite concentration method in that instead of crushing all of material 30 to less than –200 mesh, the sand particles greater than 200 mesh and the heavier pyrite minerals in material 30 are simply separated from material 30 and then added to the floated pyrite from the –200 mesh material 40.

The third method of producing pyrite concentrate 20 from clay depleted fines 30 comprises using a gravity technique such as a spiral classifier or shaker table to remove the heavier sulfide minerals from the remainder of material 30.

The tail material 32, which remains after the refractory sulfide fraction has been removed from the clay depleted fines material 30, comprises approximately 20 to 30% of the initial weight of the ore and about 5 to 10% of its gold, approximately 85% of which is recoverable in a traditional cyanide mill leaching process such as counter current decantation or carbon-in-pulp. Thus, tail material 32 is not very refractory and may be treated with clay material 26 in a traditional mill cyanide leaching process to help improve the overall recovery of the process.

After heap 18 is biooxidized, the precious metal in the pretreated ore can be extracted using a conventional lixiviant such as cyanide or thiourea, preferably cyanide. Of course, however, as a person of ordinary skill in the art would recognize, if the refractory sulfide ore is also refractory due to carbonaceous matter contained in the ore, additional processing steps must be employed to reduce the preg-robbing propensity of the ore prior to lixiviation as explained above.

EXAMPLE 1

A sample of 16 kg of refractory sulfide ore with approximately 0.04 oz/ton of gold and 3.5% of sulfide sulphur was crushed to –¼ inch. The ore sample was then separated by wet screening into a +⅛ to –¼ inch, a +30 mesh to –⅛ inch, and a –30 mesh material fractions. The –30 mesh material was further separated into a pyrite fraction, a sand fraction, and a clay fraction by gravity separation. The sand fraction was further processed by fine grinding in a ball mill for about one hour. This material was then floated with xanthate as a collector.

Each fraction was then dried and weighed and analyzed for gold. The +⅛ to –¼ inch material represented 51% of the weight and 18% of the gold at 0.48 ppm Au. The +30 mesh to –⅛ inch material represented 28% of the weight and 32% of the gold at 1.47 ppm Au. The total pyrite, which included both the gravity separated pyrite and the pyrite concentrate from the flotation of the sand, represented 4.7% of the weight and 35% of the gold at 9.8 ppm Au. The remaining sand flotation tail and clay material represented 16% of the weight and 14.6% of the gold at about 1.2 ppm Au.

The +⅛ to –¼ inch material and the +30 mesh to –⅛ inch material were combined according to their weight percentages. The combined material was adjusted to a pH of 2.0 with 10% sulfuric acid at 30 ml/kg. The one mixture was then poured into a column and aerated from the bottom with at least 15 l of air/min/m$^2$ and liquid dilute basal solutions of $(NH_4)_2SO_4$ 0.04 g/l $MgXO_4 \cdot 7H_2O$ at 0.04 g/l and $KH_2PO_4$ at 0.004 g/l were added to the top at about 15 ml/hour. *Thiobacillus ferrooxidans* bacteria were added to the top of the column and washed into the column with the liquid flow. This procedure allowed for good air flow and liquid flow and also migration of bacteria through the column. After about one month the effluent from the column showed good bioleaching of iron at about 0.1% per day.

EXAMPLE 2

A second sample of ore from the same mine as in Example 1 was crushed to –⅜ inches. Four 23 Kg splits of this sample were combined and wet screened into a +¼ inch, a +⅛ to –¼ inch, a +10 mesh to –⅛ inch, a +16 mesh to –10 mesh, a +30 to –16 mesh, a +60 to –30 mesh, and a –60 mesh fraction. The +60 to –30 mesh and the –60 mesh fraction were used to evaluate a number of gravity separations to make a pyrite fraction a sand fraction and a clay fraction. The dry weights of each size fraction were used to calculate the weight percentage of the size fraction. Each size fraction was also analyzed for the amount of gold, iron and gold extraction by traditional cyanide leaching (see Table 1).

Figure 2:
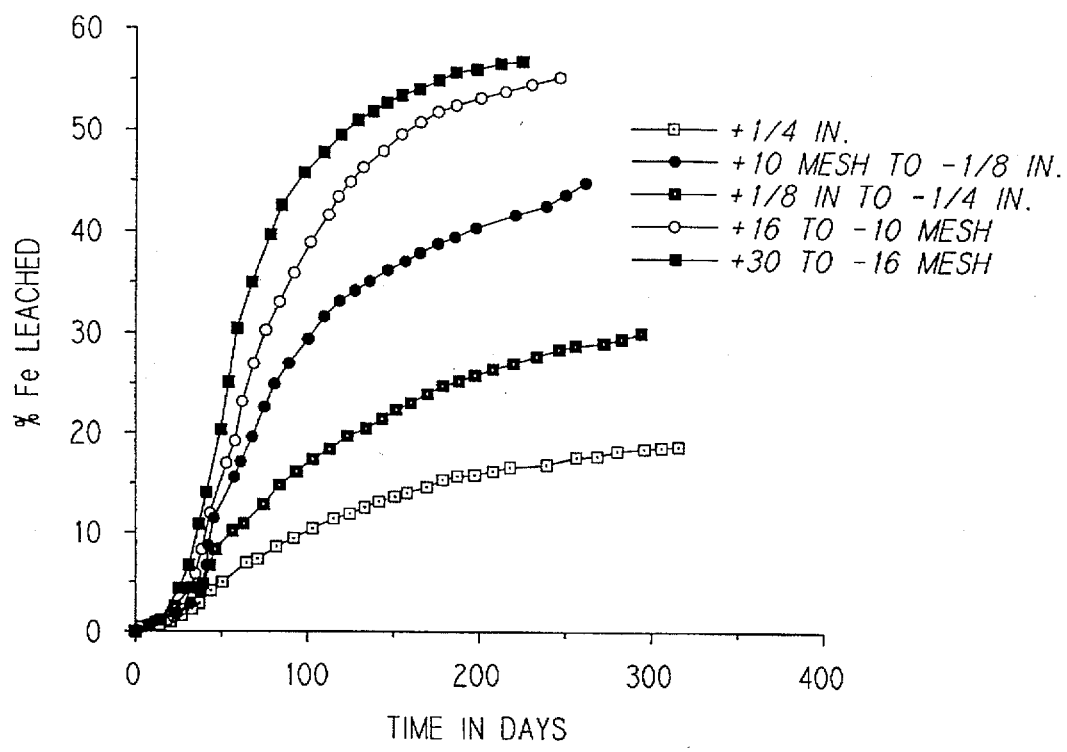
FIG. 2 is a graph illustrating the percent iron leached over time for various size fractions of ore.
Figure 3:
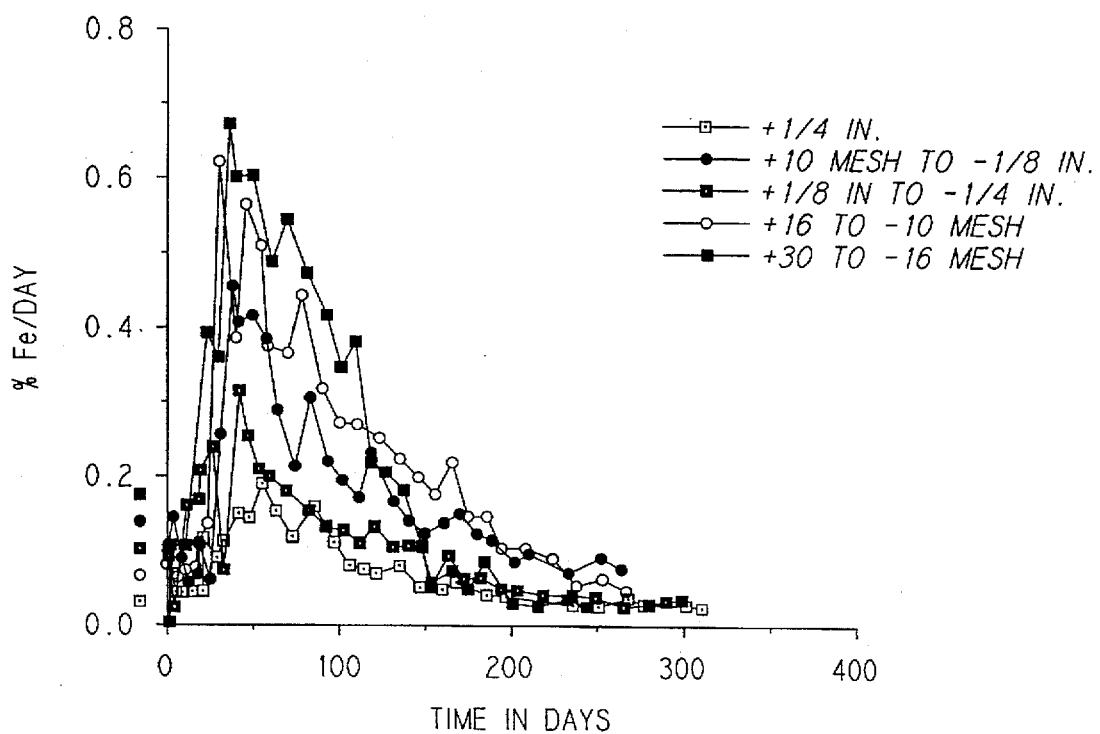
FIG. 3 is a graph illustrating the percent iron leached per day as a function of time for various size fractions of ore.

The five size fractions larger than 30 mesh were put into individual columns for biooxidation. Bacteria and nutrients were added as in Example 1 and air was blown in from the bottom or top of the column. The progress of the biooxidation was monitored by measuring the amount of iron leached from the ore by using atomic absorption analysis of the nutrient solution passing through the column. The approximate total amount of iron in each size fraction of the ore was calculated from the weight of the size fraction and an iron analysis of a representative sample of the ore. The percent iron leached and the average percent iron leached each day are plotted against time for all five size fractions in FIGS. 2 and 3, respectively.

TABLE 1

ORE SIZE FRACTION ANALYSIS

| SIZE | WT % | GRAVITY SEPARATION (wt %) | Au (ppm) | Fe % | Au % REC. | BIOOX. % RECOV. |
|---|---|---|---|---|---|---|
| +¼ | 20.9 | | 0.57 | 2.4 | 24.3 | 50.6 (15) |
| ⅛–¼ | 32.3 | | 0.78 | 2.6 | 38.8 | 62.7 (24) |
| 10–⅛ | 4.89 | | 0.525 | 3.8 | 47.3 | 76.1 (40) |
| 16–10 | 8.49 | | 1.22 | 3.8 | 44.3 | 74.7 (46) |
| 30–16 | 9.36 | | 1.92 | 5.8 | 37.3 | 84.4 (53) |
| 60–30 | 6.65 | pyrite 1.6% | 13.56 | | 47.1 | |
| | | sand 5.02% | 0.43 | | 75.3 | |
| −60 | 17.3 | pyrite 2.68% | 7.81 | | 69.9 | |
| | | clay 14.62% | 1.48 | | 86.5 | |

Au (ppm) = Concentration of gold in size fraction
Fe % = Concentration of Fe in size fraction in weight percent.
Au % Rec. = Percent gold recovered from size fraction by performing a traditional cyanide leach test without biooxidizing ore first.
Bioox. % Recov. = Percent gold recovered by cyanide leach after biooxidation. The percent of biooxidation for each sample is given in parentheses.

After several months of biooxidation, samples were taken from each column and the percent iron leached noted. The partially biooxidized ore was then leached with cyanide in the same way the original unoxidized samples were. The gold extraction of the unoxidized sample and the biooxidized sample are compared in Table 1. The percent biooxidation for each size fraction is reported in Table 1 in parentheses. From this data one can see that the smaller size fractions biooxidized at a faster rate. Also, all the size fractions show an increase in gold extraction after being biooxidized.

The +60 to −30 mesh and −60 mesh size fractions were also analyzed for gold extraction. The sand tails from a shaker table separation of the refractory pyrite from the +60 to −30 mesh fraction was fairly low in gold, but the gold was cyanide extractable without biooxidation (75%). The very fine sand and clay from the −60 mesh fraction was higher in gold and in gold extraction (86%). This indicated that no further oxidation of the very fine sand and clay materials in this size fraction was required.

The removal of the small size fractions (i.e., the size fractions having a particle size less than 30 mesh) including the clay fraction allowed all the columns to have excellent air flow. Columns made with whole ore or whole ore with agglomeration often would become plugged, inhibiting air flow. Thus, by separating the fines and clays, large scale heaps may be constructed without having to use larger crush sizes (i.e., ¾ inch or larger) to achieve good air flow.

Figure 4:
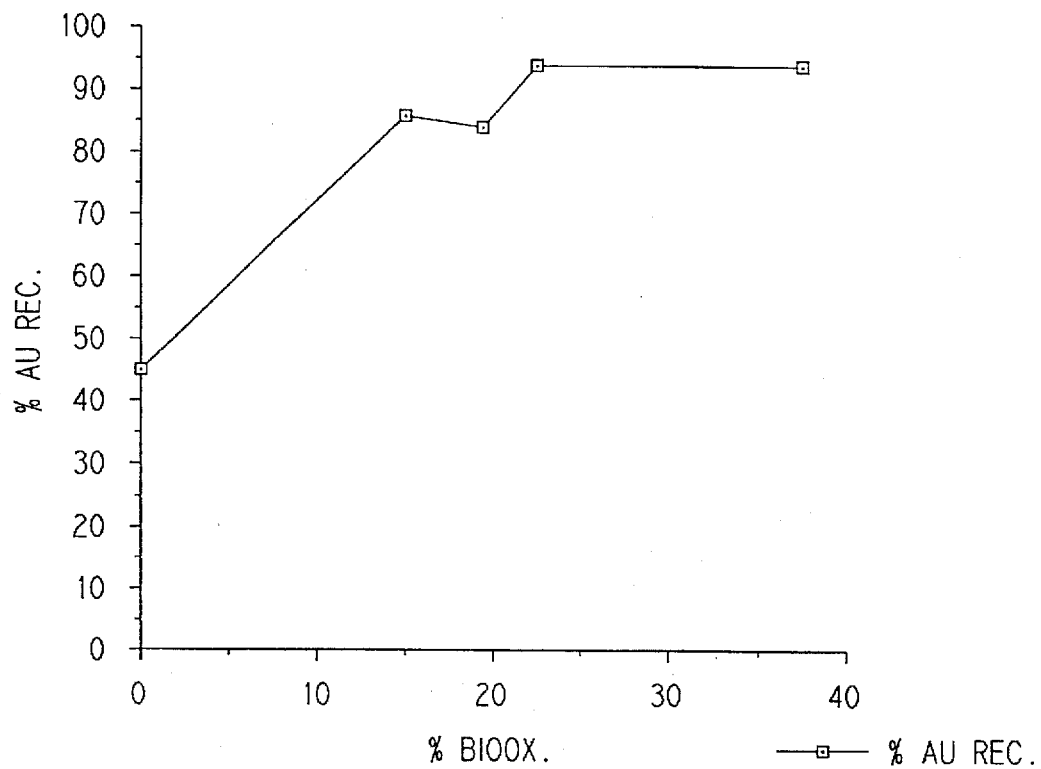
FIG. 4 is a graph illustrating the percent gold recovered from a pyrite concentrate milled to −200 mesh as a function of its percent biooxidation.

The pyrite fractions of the −30 and −60 mesh fractions were both high in gold and refractory to cyanide leaching. These pyrite fractions were combined and then milled to −200 mesh in a ball mill. The −200 mesh pyrite concentrate was used in shake flask experiments to determine the amount of gold extraction as a function of percent biooxidation (see FIG. 4). In preparing these tests, 75 ml of a 500 ppm cyanide solution was added to 30 gm of the pyrite concentrate. The solution and ore was then rolled at 10 rpm for 96 hrs. before the cyanide solution was tested to determine the amount of gold extracted.

Some of the pyrite from the gravity separated fines was further processed by grinding to −200 mesh and floating with xanthate to from a concentrate of over 50% pyrite. A sample of this concentrate weighing 500 gm was then mixed with 500 ml of solution containing iron oxidizing bacteria at greater than $10^8$ cells per ml and 3000 ppm ferric sulfate.

After one hour, the 500 gm sample of pyrite concentrate suspended in 500 ml of ferric-bacteria solution was poured directly onto the top of the +¼ inch ore column, containing about 15 Kg of ore. This was done after biooxidation of the column ore had been in progress for over 300 days. The black liquid spread quickly down through the column with most of the pyrite concentrate being retained by the column. The small amount of pyrite concentrate that did pass through the column was poured back onto the top of the column and was retained by the column on the second pass. The pyrite appeared to be evenly distributed throughout the column and did not inhibit the air flow.

Figure 5:
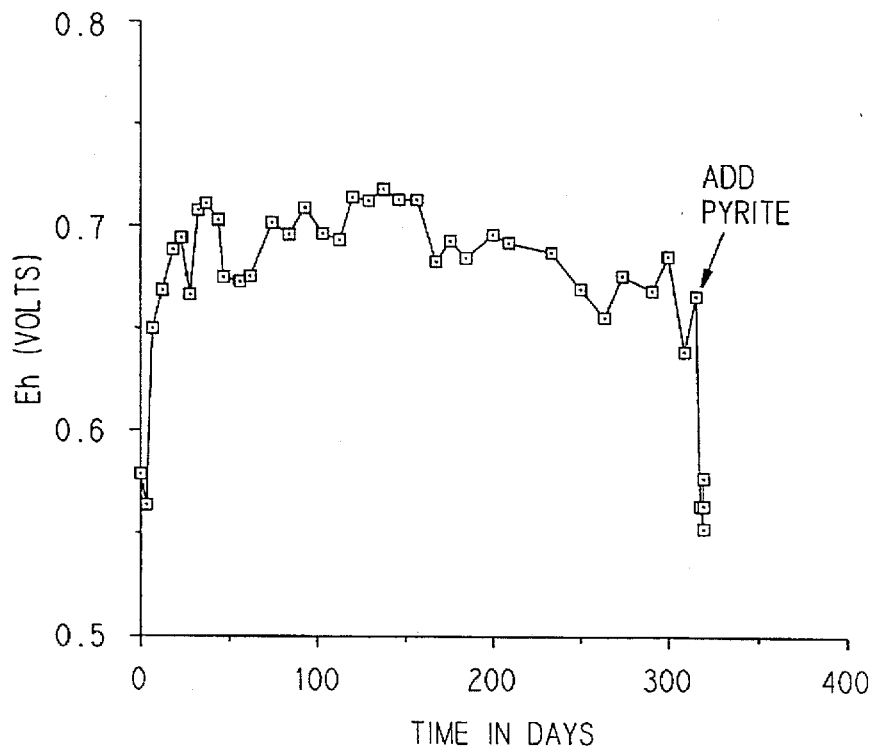
FIG. 5 is a graph illustrating the change in Eh of a column of +¼ inch ore as a function of time.
Figure 6:
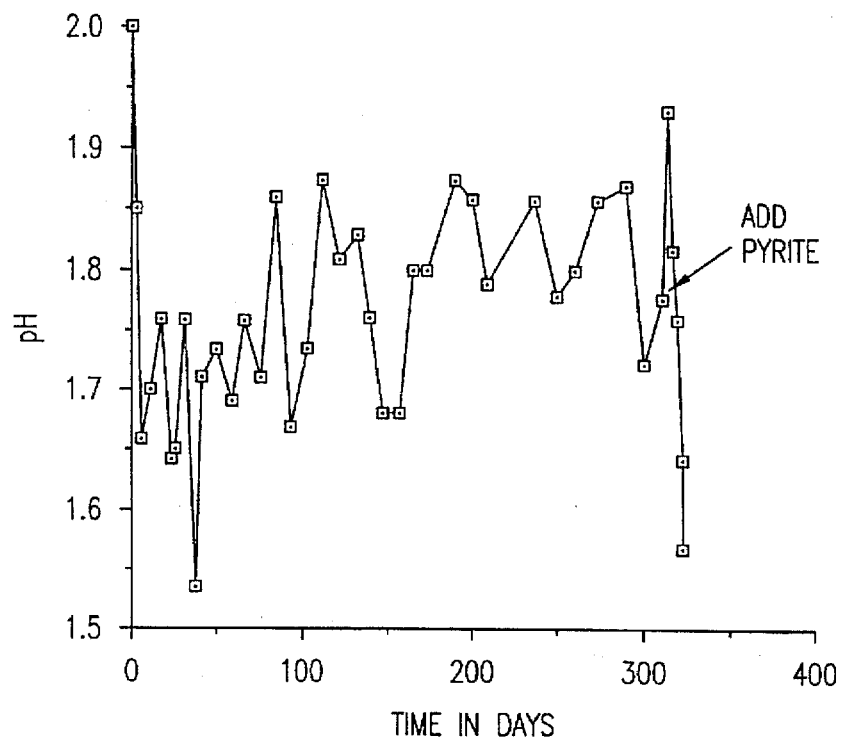
FIG. 6 is a graph illustrating the change in pH as a function of time for a column of +¼ inch ore.
Figure 7:
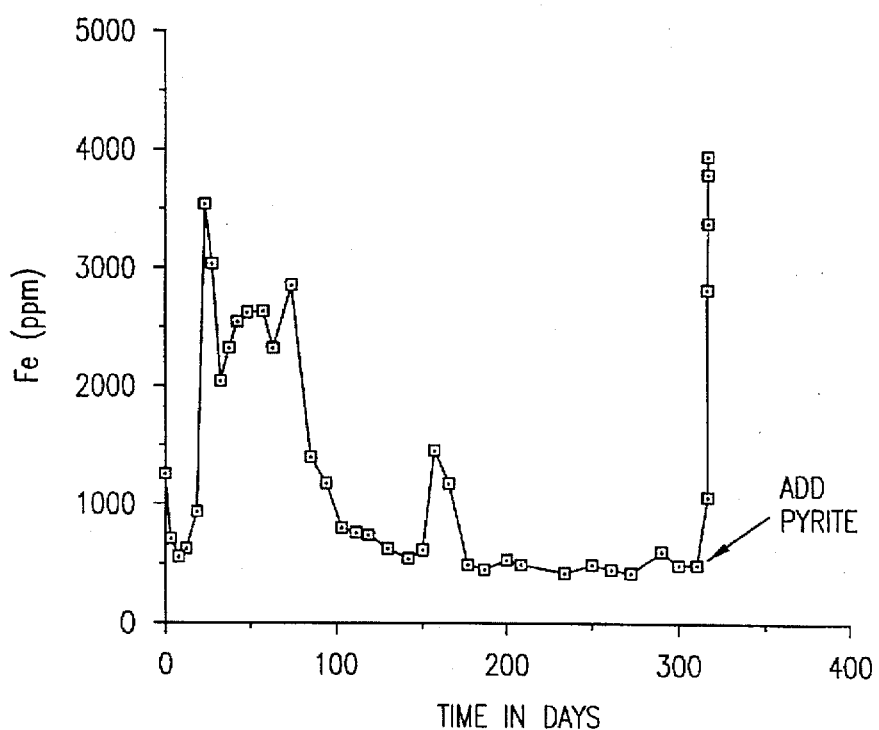
FIG. 7 is a graph illustrating the change in iron concentration in the effluent of a column of +¼ inch ore as a function of time.

Liquid at pH 1.8 was dripped onto the top of the column, as had been done throughout the experiment. The flow rate was about 200 ml per day. The liquid collected after three days had dropped in Eh from about 650 mV to 560 mV. The pH was still at about 1.8 as it had been for a long time. The iron concentration in the liquid was 2800 ppm, which was just a little lower than the iron concentration of the added bacteria solution. Two days after adding the pyrite concentrate to the column, the iron concentration in the off solution had increased to 4000 ppm and the pH had dropped to 1.6 indicating that biooxidation of the pyrite had started. FIGS. 5, 6, and 7 illustrate the change in Eh, pH, and iron concentration of the column effluent, respectively over time.

Another aspect of the present invention will now be described. In this aspect, a process for recovering precious metal values from a concentrate of precious metal bearing refractory sulfide minerals is described. The process comprises (a.) distributing a concentrate of refractory sulfide minerals on top of a heap of support material; (b.) biooxidizing the concentrate of refractory sulfide minerals; (c.) leaching precious metal values from the biooxidized refractory sulfide minerals with a lixiviant; and (d.) recovering precious metal values from the lixiviant.

A concentrate of precious metal bearing refractory sulfide minerals will typically be prepared from a precious metal bearing refractory sulfide ore. The concentrate can be prepared from such ores using well known gravity separation or flotation techniques. Although gravity separation is cheaper, flotation is the preferred method of separation because of the selectivity of the process. The most frequently used collector for concentrating sulfide minerals in a flotation process is Xanthate. Xanthate flotation processes are well known to those skilled in the art and need not be described in detail herein.

Preferably the particle size of the concentrate is such that 80 to 90% of the concentrate is less than 100 to 300 mesh. More preferably, 80 to 90% of the concentrate is less than 100 to 150 mesh.

The optimum size may, however, vary with various ore types. In general, the operator should strive for a particle size which permits optimum separation in the concentration process and which provides for the optimal rate of biooxidation versus the incremental costs of additional fine grinding.

The smaller the particle size of the sulfide minerals within the concentrate, the more quickly the concentrate will oxidize during bioleaching. However, the faster biooxidation rate does not always justify the added energy costs associated with fine grinding an ore or a flotation concentrate.

With the process according to the present invention, the cost of leaving the concentrate on the heap to biooxidize is minimal. Therefore, a slightly longer biooxidation period may be justified to avoid having to incur additional grinding related expenses. In this regard, the present process has an advantage over mill type processes. In mill type processes, the sulfide mineral concentrate must be very finely ground to ensure high biooxidation rates so that the bioreactor can process as much concentrate as possible in as short of period of time as possible to maintain the economics of the process.

After the sulfide mineral concentrate is formed, it is distributed over the top of a heap of support material. Preferably, the concentrate is distributed on top of the heap in a slurry form so that the concentrate can be piped directly to the heap without having to be dried first. The pulp density of the concentrate should be adjusted so that the concentrate flows well, but does not simply wash through the heap of support material. Because the sulfide mineral particles are hydrophobic, they will tend to stick to the support material rather than migrating completely through the heap if the appropriate support material is selected. Nor should blockage of flow channels be a problem if an appropriate size support material is selected.

The purpose of the support material is to capture and retain the sulfide minerals as they slowly migrate down through the heap so that the support material acts as a large surface area bioreactor. For this reason support materials having a high degree of porosity or a rough surface are preferred since these types of surfaces will tend to capture and retain the concentrate. The more concentrate that the support rock can support without blockage of the flow channels the better. Support materials that can be used in practicing the present invention include coarse ore particles, lava rock, gravel, or rock containing small amounts of mineral carbonate as a source of $CO_2$ for the biooxidizing bacteria. Lava rock is a particularly preferred support material due to its roughness and high degree of porosity.

Support material which contains a small amount of mineral carbonate is beneficial not only for the $CO_2$ that it produces but is also beneficial because it will help buffer the acid solution produced as a result of the biooxidation process. This will make it easier to control the pH of the bioreactor during the biooxidation process.

With respect to selection of an appropriate size of support material, there are several competing interests that should be considered. Smaller diameter support materials have greater surface area and thus increase the effective area of the bioreactor created by the heap of support material. However, smaller diameter support material may be more expensive depending on the amount of grinding required to produce the desired size. Further, smaller diameter support material may be subject to more blockage of fluid flow channels by the concentrate which is added to the top of the heap. Larger support material will permit taller heaps to be formed without risk of flow channels becoming plugged.

Typically, the support material will be larger than about ¼ inch in diameter and smaller than about 1 inch in diameter. Preferably the support material is greater than about ⅜ inch in diameter and less than about ¾ inch in diameter. A support material having a diameter of about ½ inch should be the optimum size.

To biooxidize the concentrate, the heap is inoculated with bacteria or other microbe capable of biooxidizing the sulfide minerals in the concentrate. Such microbial treatments are well known in the art. Bacteria that can be used for this purpose include *Thiobacillus ferrooxidans, Leptospirillum ferrooxidans,* and *Thiobacillus thiooxidans. Thiobacillus ferrooxidans* is an especially preferred microorganism for biooxidation processes.

If the bioleachate solution is recycled, precautionary steps may be required to prevent toxic materials from building up in the recycled solution so that the rate of biooxidation is not retarded significantly. The process described in U.S. patent application Ser. No. 08/329,002, filed Oct. 25, 1994, can be used to ensure that inhibitory materials do not build up to the point that they become detrimental to the biooxidation process.

After the refractory sulfide concentrate is sufficiently biooxidized, the liberated precious metal values can be leached with a lixiviant of thiourea or cyanide. Cyanide is the preferred lixiviant even though the pH of the heap must first be raised prior to leaching. An advantage of thiourea is that it is not toxic to the biooxidizing microorganisms. As a result, intermittent leachings can be performed to dissolve the liberated precious metal values and then the biooxidation process can be resumed.

Dissolved precious metal values can be recovered from the lixiviant using well known techniques to those skilled in the art such as carbon in leach and carbon in column processes.

Another advantage of the present process is that it can be used as a continuous process by intermittently adding fresh or new concentrate to the top of the heap. The advantage of adding fresh concentrate to the top of the heap is that once the heap is established and biooxidation is occurring rapidly, the fresh concentrate can be added to maintain the high rate of biooxidation within the heap without having to tear down the heap to process the biooxidized material.

Due to the relatively low capital and operating costs of the present process, it can be used to economically process much lower grade concentrates, and as a result lower grade ores, than a mill biooxidation process. Further, by distributing the concentrate of precious metal bearing refractory sulfide minerals on top of a heap of support material, good fluid flow (both air and liquid) is ensured within the heap.

Another aspect of the present invention is now described. In this aspect, a process is provided for recovering base metal values from sulfide ores. Such ores include, by way of example, chalcopyrite, sphalorite, nickel sulfide ores, and uranium sulfide ores. The process according to this aspect of the invention comprises (a.) forming a concentrate of metal sulfide minerals; (b.) spreading the concentrate on top of a heap of support material; (c.) biooxidizing the concentrate; and (d.) recovering metal values from the solution used to biooxidize the metal sulfide minerals. Due to the fact that this process, like the process previously described for processing concentrates of precious metal bearing sulfide minerals, uses a heap of support material for the bioreactor, its capital and operating costs are less than that of a mill bioleaching operation. However, due to the good air flow in the heap, the biooxidation rate of the sulfide minerals is quite high and can approach that of what would be observed in a mill type operation.

Depending on the sulfide ore from which the concentrate is obtained, the base metal values that can be recovered from the process according to the present aspect of the invention include copper, zinc, nickel and uranium.

The process parameters and considerations for the process according to the present aspect are much the same as those set forth above for the method of processing precious metal bearing concentrates of refractory sulfide minerals. The primary difference between the two processes, however, is that the base metal values of interest in the present process dissolve during the biooxidation process. As a result, the metal values are recoverable directly from the solution used to biooxidize the concentrate of metal sulfide minerals. The technique used to extract the metal values of interest will depend on the specific metal of interest. As those skilled in the art will immediately recognize, such techniques may include solvent extraction, iron cementation, and precipitation through pH adjustments. Solvent extraction is a particularly preferred method of removing copper from the bioleachate solution.

As with the above described process for recovering precious metal values from a precious metal bearing concentrate of sulfide minerals, the present process can be operated in a continuous mode by adding concentrate on an intermittent basis. For example, concentrate can be added on a daily or weekly basis. As described above, such additions will ensure that the rate of biooxidation remains high for the concentrate that is distributed over the heap and which has migrated through the heap.

As one skilled in the art will recognize, the process according to the present aspect of the invention can be combined with the above process for recovering precious metal values from a concentrate of refractory sulfide minerals. This is because base metal values from the refractory sulfide minerals will inherently dissolve into the bioleachate solution during the biooxidation process while simultaneously liberating any occluded precious metal values contained in the sulfide minerals. These values can then be recovered if desired using the techniques described above.

EXAMPLE 3

Two simultaneous bioleaching tests were set up to test the rate of biooxidation of a gold bearing ore pyrite concentrate. The first test consisted of a column type experiment to simulate a heap leaching process and the second consisted of a shake flask experiment to simulate a stirred tank process.

The starting concentrate for both tests was obtained from the Jamestown mine in Tuolumne County, Calif. The mine is owned by Sonora Gold corporation and lies along the mother lode vein system. The concentrate was produced using a xanthate flotation process and contained 39.8% sulfides and 36.6% iron. The sulfide minerals within the concentrate primarily consisted of pyrite. Size analysis showed that over 76% of the concentrate particles were smaller than 200 mesh. The concentrate had a high gold concentration (about 2 oz. per ton of concentrate) and was known to be refractory to cyanide leaching.

The percentage of biooxidation in each of the tests was determined by analysis of the iron concentration in all solutions removed from the column or in the case of the flask experiment the concentration of iron in solution plus any iron solution removed.

A culture of *Thiobacillus ferrooxidans* was used to biooxidize the sulfide mineral concentrate in each of the tests. The culture of *Thiobacillus ferrooxidans* was originally started with ATCC strains 19859 and 33020. The culture was grown in an acidic nutrient solution having a pH of 1.7 to 1.9 and containing 5 g/l ammonium sulfate (($NH_4)_2SO_4$)), 0.833 g/l magnesium sulfate heptahydrate ($MgSO_4.7H_2SO_4$), and 20 g/l iron in the form of ferrous and ferric sulfate. The pH of the solution was adjusted to the above range using sulfuric acid ($H_2SO_4$).

Prior to application of the culture to the test samples, the mixed culture of sulfide mineral oxidizing bacteria was grown to a cell density of $4 \times 10^9$ to $1 \times 10^{10}$ cell per ml.

The column experiment was started by inoculating a 150 g sample of concentrate with about $10^8$ cells per gram of concentrate. This was accomplished by adding three milliliters of bacteria at $5 \times 10^9$ cells per milliliter to the 150 g sample of pyrite concentrate. The 150 g of pyrite concentrate suspension was then poured into a 3 inch by 6 foot column filled about halfway with 3 liters of ⅜ inch lava rock. The lava rock support material was chosen because it has a high surface area and it holds up well to the acid condition encountered during biooxidation.

During inoculation and subsequent solution additions, the pyrite concentrate did not wash out of the column. Most of the pyrite concentrate was held in the first foot of the lava rock. Air and liquid were introduced through the top of the column. The bioleach solution was recirculated until the pH of the column was adjusted down to about 1.8. After biooxidation started within the column, a 0.2×9K salts solution having a pH of 1.8 and containing 2000 ppm of iron, primarily in the ferric form, was fed to the column. The 2,000 ppm of iron was subtracted from all analysis of iron in solution coming off of the column.

The composition of the standard 9K salts medium for *T. ferrooxidans* is listed below. The concentrations are provided in grams/liter.

| | |
|---|---|
| $(NH_4)SO_4$ | 5 |
| KCl | 0.17 |
| $K_2HPO_4$ | 0.083 |
| $MgSO_4.7H_2O$ | 0.833 |
| $Ca(NO_3).4H_2O$ | 0.024 |

The notation 0.2×9K salts indicates that the 9K salt solution strength was at twenty percent that of the standard 9K salts medium.

After 26 days of biooxidation, about 35% of the iron in the pyrite concentrate had been oxidized. At this point, the test was converted to a continuous process test by adding 3 g of new concentrate to the column every day. After 9 more days, the rate of pyrite addition was increased to 6 g per day.

The flask experiment was started at the same time as the column experiment. To start the experiment, a 50 g sample of the pyrite concentrate was inoculated with 1 milliliter of the bacteria culture. The pyrite concentrate was then added to 1 liter of 0.2×9K salts solution having a pH of 1.8 in a large shake flask. Not only was the concentrate inoculated with the same bacteria, but it was also inoculated at the same number of cells per gram.

Air was introduced to the bioleach solution by orbital shaking of the flask at about 250 rpm. Solution was removed from the flask from time to time to keep the ferric concentration from getting much higher than that in the column.

When the column experiment was converted to a continuous process on day 26, the flask experiment was also converted to a continuous test by adding 1 g of pyrite concentrate per day to the flask. After 9 more days, the amount of concentrate added was increased to 2 g per day.

After 58 days, the pyrite additions to both the flask and column experiments were stopped. Both the column and the flask were then allowed to biooxidize an additional 20 days. At this point, the concentrate in the column was about 76% oxidized and the concentrate in the flask was about 89% oxidized. The column was then leached for 10 days with thiourea to extract liberated gold. The thiourea only extracted about 30% of the gold. However, after 3 days of reverting back to additions of the 0.2×9K salts solution having a pH of 1.8 and containing 2,000 ppm of ferric iron, the Eh and the iron concentration of the column effluent increased. This indicated that the thiourea was not toxic to the bacteria and that thiourea extractions could be done from time to time without killing the bacteria.

Figure 8:
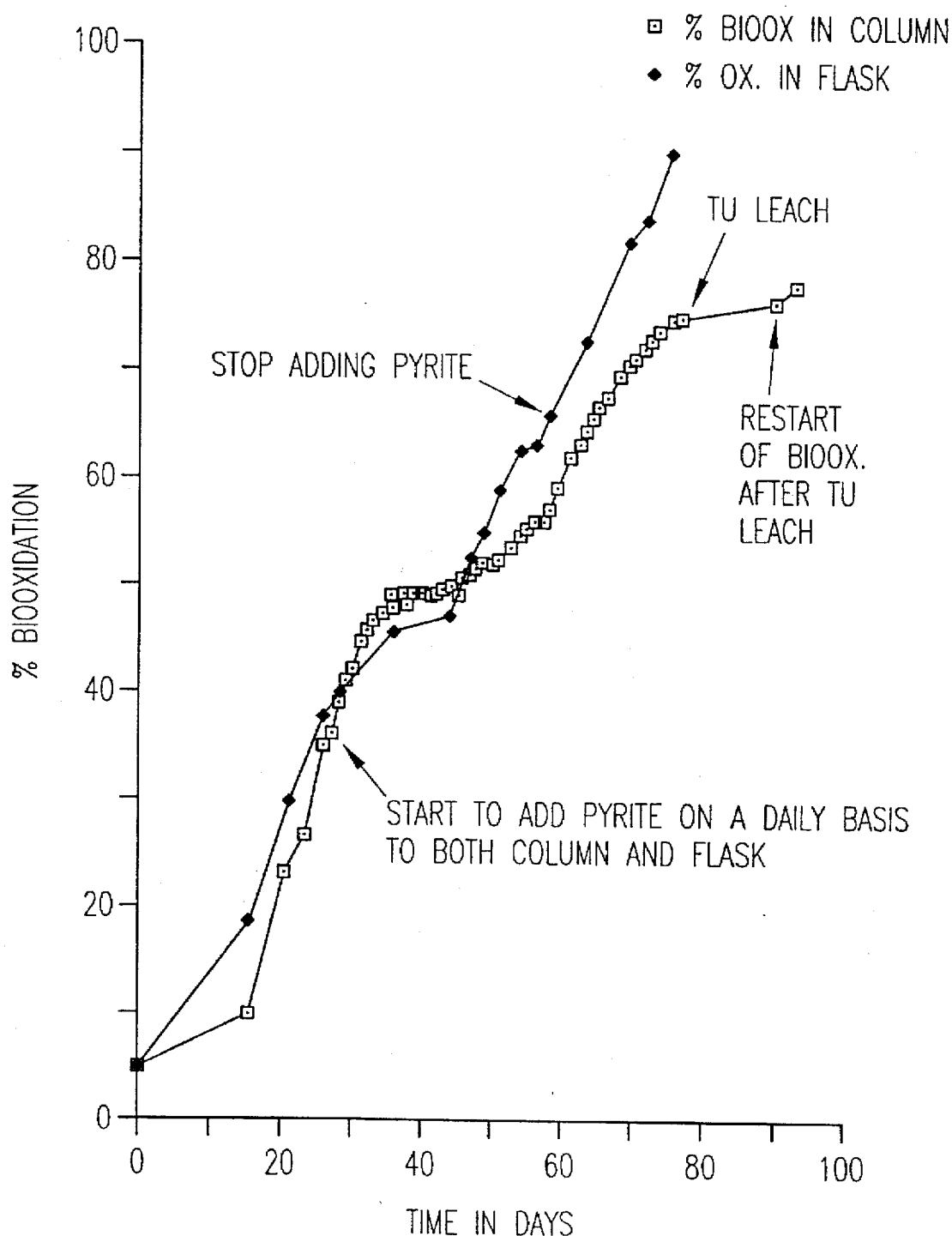
FIG. 8 is a graph illustrating the biooxidation rate for a concentrate on lava rock process according to the present invention versus a stirred tank type process.

FIG. 8 shows the amount of biooxidation versus time in days for both the column and flask concentrate bioleaching tests. The phrase "TU leach" in FIG. 8 stands for thiourea leach. The data used to prepare FIG. 8 is tabulated in Tables 2 and 3 at the end of this example.

As indicated above, the flask was meant to simulate a stirred tank process. When the flask test was converted to a continuous process by adding pyrite each day, it was meant to simulate a large scale process in which new pyrite is introduced on an intermittent basis to a rapidly biooxidizing tank containing a large amount of bacteria that have adapted to the ore. The daily addition of pyrite to the column was done to test the feasibility of a continuous process in which a concentrate of precious metal bearing sulfide minerals is continuously or intermittently added to the top of a heap comprised of biooxidizing concentrate distributed on a heap of support material such as lava rock.

As the above tests demonstrate, the rates of biooxidation were not significantly different between the column and flask tests. The start of biooxidation was a little slower in the column test. This may have been due to about a 10 day lag time in adjusting the pH of the column down to 1.8. The rate of biooxidation in the column then picked up to be the same as the flask. Later in the experiment the rate began to slow down again. This may have been due to a lack of mixing of the fresh pyrite with the biooxidizing pyrite. However, the rates of biooxidation between the two tests were close enough to demonstrate the viability of the process according to the present invention. The viability of the present process is especially attractive in view of the much lower capital and operating costs of a heap process as compared to a stirred tank process.

TABLE 2

Data From Column Biooxidation Test

| Time in days | G. of iron added to column | Total g. of iron removed | % bioox. of pyrite based on iron | Conc. of iron in g./l |
|---|---|---|---|---|
| 0 | 54.400 | 2.830 | 5.200 | 1.884 |
| 15 | 54.400 | 5.500 | 10.100 | 2.840 |
| 20 | 54.400 | 12.617 | 23.180 | 4.704 |
| 23 | 54.400 | 14.480 | 26.620 | 4.976 |
| 26 | 55.540 | 19.230 | 34.620 | 9.088 |
| 27 | 56.630 | 20.430 | 36.070 | 9.432 |
| 28 | 57.720 | 22.329 | 38.700 | 9.800 |
| 29 | 58.800 | 23.987 | 40.800 | 6.400 |
| 30 | 59.900 | 25.176 | 42.000 | 5.964 |
| 31 | 61.000 | 27.075 | 44.380 | 5.876 |
| 32 | 62.070 | 28.337 | 45.650 | 6.508 |
| 33 | 63.160 | 29.285 | 46.360 | 6.212 |
| 34 | 64.250 | 30.257 | 47.080 | 4.900 |
| 35 | 65.340 | 31.824 | 48.700 | 7.224 |
| 36 | 69.700 | 32.970 | 47.300 | 5.428 |
| 37 | 69.700 | 34.066 | 48.900 | 5.265 |
| 38 | 74.050 | 35.184 | 47.500 | 5.620 |
| 39 | 74.050 | 36.302 | 49.000 | |
| 40 | 76.230 | 37.420 | 49.100 | 5.120 |
| 41 | 78.410 | 38.425 | 49.000 | 5.000 |
| 42 | 80.590 | 39.453 | 48.900 | 5.024 |
| 43 | 82.760 | 40.744 | 49.200 | 5.536 |
| 44 | 84.940 | 42.172 | 49.600 | 5.808 |
| 45 | 89.300 | 43.602 | 48.800 | 5.964 |
| 46 | 89.300 | 45.032 | 50.400 | |
| 47 | 91.480 | 46.462 | 50.800 | 5.976 |
| 48 | 93.660 | 47.932 | 51.180 | 6.200 |
| 49 | 95.836 | 49.650 | 51.800 | 6.896 |
| 50 | 98.014 | 50.582 | 51.600 | 7.328 |
| 51 | 100.192 | 52.142 | 52.040 | 8.240 |
| 53 | 104.548 | 55.591 | 53.170 | 9.664 |
| 54 | 106.726 | 58.012 | 54.360 | 8.052 |
| 55 | 108.896 | 59.835 | 64.950 | 8.288 |
| 56 | 111.066 | 61.571 | 55.440 | 8.200 |

TABLE 2-continued

Data From Column Biooxidation Test

| Time in days | G. of iron added to column | Total g. of iron removed | % bioox. of pyrite based on iron | Conc. of iron in g./l |
|---|---|---|---|---|
| 57 | 113.236 | 63.136 | 55.760 | 7.304 |
| 58 | 115.406 | 65.370 | 56.640 | 8.384 |
| 59 | 115.406 | 67.640 | 58.610 | 8.484 |
| 61 | 115.406 | 70.806 | 61.350 | 8.208 |
| 62 | 115.400 | 72.344 | 62.690 | 7.128 |
| 63 | 115.400 | 72.777 | 63.930 | 6.776 |
| 64 | 115.400 | 75.013 | 65.000 | 5.852 |
| 65 | 115.400 | 76.169 | 66.000 | 5.728 |
| 66 | 115.406 | 77.325 | 67.000 | 5.728 |
| 68 | 115.406 | 79.668 | 69.030 | 5.748 |
| 69 | 115.406 | 80.468 | 69.730 | 4.668 |
| 70 | 115.400 | 81.043 | 70.220 | 4.740 |
| 71 | 115.400 | 81.828 | 70.904 | 4.856 |
| 72 | 115.400 | 82.716 | 71.674 | 5.064 |
| 73 | 115.400 | 83.781 | 72.590 | 4.804 |
| 75 | 115.400 | 84.975 | 73.630 | 4.488 |
| 76 | 115.400 | 85.609 | 74.180 | 4.112 |
| 90 | 115.400 | 87.170 | 75.533 | 2.892 |
| 93 | 115.400 | 88.754 | 76.900 | 3.476 |

TABLE 3

Flask Biooxidation Data

| Time in days | Flask % bioox. by iron |
|---|---|
| 0 | 4.930 |
| 15 | 18.890 |
| 21 | 29.850 |
| 26 | 37.400 |
| 28 | 39.790 |
| 36 | 45.370 |
| 44 | 46.890 |
| 47 | 52.310 |
| 49 | 54.510 |
| 51 | 58.380 |
| 54 | 62.010 |
| 56 | 62.630 |
| 58 | 65.400 |
| 63 | 72.110 |
| 69 | 81.410 |
| 72 | 83.300 |
| 75 | 89.440 |

Although the invention has been described with reference to preferred embodiments and specific examples, it will readily be appreciated by those of ordinary skill in the art that many modifications and adaptions of the invention are possible without departure from the spirit and scope of the invention as claimed hereinafter. For example, while some of the processes according to the present invention have been described in terms of recovering gold from refractory sulfide or refractory carbonaceous sulfide ores, the processes are equally applicable to other precious metals found in these ores such as silver and platinum.

I claim:

1. A process for recovering precious metal values from a concentrate of precious metal bearing refractory sulfide minerals having a particle size of 80 to 90% less than 100 mesh, said process comprising:

a. distributing the concentrate of refractory sulfide minerals on top of a heap of coarse support material;

b. biooxidizing the concentrate of refractory sulfide minerals;

c. leaching precious metal values from the biooxidized refractory sulfide minerals with a lixiviant; and d. recovering precious metal values from the lixiviant.

2. A process according to claim 1, wherein the precious metal recovered from the lixiviant is at least one selected from the group consisting of gold, silver and platinum.

3. A process according to claim 1, wherein the precious metal recovered from the lixiviant is gold.

4. A process according to claim 1, wherein the support material is selected from the group consisting of lava rock, gravel, and coarsely ground ore.

5. A process according to claim 1, wherein the support material is lava rock.

6. A process according to claim 1, wherein the lixiviant is selected from the group consisting of thiourea and cyanide.

7. A process according to claim 1, wherein the lixiviant is thiourea.

8. A process according to claim 1, further comprising adding fresh concentrate to the top of the heap on an intermittent basis.

9. A process according to claim 8, wherein the precious metal values are intermittently leached from the biooxidized refractory sulfide minerals with thiourea.

10. A process for recovering precious metal values from a concentrate of precious metal bearing refractory sulfide minerals having a particle size of 80 to 90% less than 100 mesh, said process comprising:

a. distributing the concentrate of refractory sulfide minerals on top of a heap of coarse support material, wherein the support material is selected from the group consisting of lava rock, gravel, and coarsely ground ore;

b. biooxidizing the concentrate of refractory sulfide minerals;

c. leaching precious metal values from the biooxidized refractory sulfide minerals with a lixiviant; and d. recovering precious metal values from the lixiviant.

11. A method according to claim 10, wherein the precious metal recovered is selected from the group consisting of gold, silver, and platinum.

12. A method according to claim 10, wherein the lixiviant is selected from the group consisting of thiourea and cyanide.

13. A process according to claim 10, further comprising adding fresh concentrate to the top of the heap on an intermittent basis.

14. A process according to claim 10, wherein the precious metal values are intermittently leached from the biooxidized refractory sulfide minerals with thiourea.

15. A process for recovering gold values from a concentrate of gold bearing refractory sulfide minerals having a particle size of 80 to 90% less than 100 mesh, said process comprising:

a. distributing the concentrate of refractory sulfide minerals on top of a heap of coarse support material, wherein the support material is selected from the group consisting of lava rock, gravel, and coarsely ground ore;

b. biooxidizing the concentrate of refractory sulfide minerals;

c. adding fresh concentrate to the top of the heap on an intermittent basis;

d. intermittently leaching gold from the biooxidized refractory sulfide minerals with thiourea; and e. recovering gold values from the thiourea.

16. A process for recovering base metal values from a sulfide ore, comprising:

a. forming a concentrate of metal sulfide minerals having a particle size of 80 to 90% less than 100 mesh;

b. spreading the concentrate on top of a heap of coarse support material;

c. biooxidizing the concentrate; and d. recovering base metal values from the solution used to biooxidize the metal sulfide minerals.

17. A method according to claim 16, wherein the metal values recovered are selected from the group consisting of copper, zinc, nickel, and uranium.

18. A method according to claim 16, wherein the metal recovered is copper.

19. A process according to claim 16, wherein the support material is selected from the group consisting of lava rock, gravel, and coarsely ground rock.

20. A process according to claim 16, wherein the support material is lava rock.

21. A process according to claim 16, further comprising adding fresh concentrate to the top of the heap on an intermittent basis.

22. A process for recovering base metal values from a sulfide ore, comprising:

a. forming a concentrate of metal sulfide minerals having a particle size of 80 to 90% less than 100 mesh;

b. spreading the concentrate on top of a heap of coarse support material, wherein the support material is selected from the group consisting of lava rock, gravel, and coarsely ground rock;

c. biooxidizing the concentrate;

d. adding fresh concentrate to the top of the heap on an intermittent basis; and e. recovering base metal values from the solution used to biooxidize the metal sulfide minerals.

23. A process according to claim 22, wherein the support material is lava rock.

24. A process according to claim 22, wherein the metal recovered is selected from the group consisting of copper, zinc, nickel, and uranium.

25. A process according to claim 22, wherein the metal recovered is copper.

* * * * *